(12) United States Patent
Lund

(10) Patent No.: US 10,517,914 B2
(45) Date of Patent: Dec. 31, 2019

(54) HEALTHY TAN TYPE OF ANTIOXIDANT DEFENSE

(71) Applicant: Eric Lund, Irvine, CA (US)

(72) Inventor: Eric Lund, Irvine, CA (US)

( * ) Notice: Subject to any disclaimer, the term of this patent is extended or adjusted under 35 U.S.C. 154(b) by 54 days.

(21) Appl. No.: 15/706,698

(22) Filed: Sep. 16, 2017

(65) Prior Publication Data

US 2018/0078600 A1    Mar. 22, 2018

Related U.S. Application Data

(60) Provisional application No. 62/396,014, filed on Sep. 16, 2016.

(51) Int. Cl.
| | |
|---|---|
| *A61K 36/185* | (2006.01) |
| *A61K 36/82* | (2006.01) |
| *A61K 35/60* | (2006.01) |
| *A61K 31/07* | (2006.01) |
| *A61K 31/593* | (2006.01) |
| *A61K 31/355* | (2006.01) |
| *A61K 31/375* | (2006.01) |
| *A61K 31/122* | (2006.01) |
| *A61K 33/30* | (2006.01) |
| *A61K 33/34* | (2006.01) |
| *A61K 31/198* | (2006.01) |
| *A61K 31/4525* | (2006.01) |
| *G06F 19/00* | (2018.01) |

(52) U.S. Cl.
CPC .............. *A61K 36/82* (2013.01); *A61K 31/07* (2013.01); *A61K 31/122* (2013.01); *A61K 31/198* (2013.01); *A61K 31/355* (2013.01); *A61K 31/375* (2013.01); *A61K 31/4525* (2013.01); *A61K 31/593* (2013.01); *A61K 33/30* (2013.01); *A61K 33/34* (2013.01); *A61K 35/60* (2013.01); *A61K 36/185* (2013.01); *G06F 19/326* (2013.01); *G06F 19/3456* (2013.01)

(58) Field of Classification Search
None
See application file for complete search history.

(56) References Cited

U.S. PATENT DOCUMENTS

| | | | | |
|---|---|---|---|---|
| 2006/0112584 | A1* | 6/2006 | Jones | A23B 7/02 34/60 |
| 2006/0292094 | A1* | 12/2006 | Bell | A61K 8/02 424/59 |
| 2008/0305096 | A1* | 12/2008 | Verdegem | A61K 9/148 424/94.4 |
| 2010/0080762 | A1* | 4/2010 | Goralczyk | A61K 8/31 424/59 |

OTHER PUBLICATIONS

Chen, A. et al. Oral and Systemic Photoprotection. Photodermatology, Photoinnnnunity & Photomedicine 30(2-3)102-111, Apr./Jun. 2014. (Year: 2014).*
Jackson M. et al. Effects of Micronutrient Supplements on UV Induced Skin Damage. Proceedings of the Nutrition Society 61(2)187-189, 2002. (Year: 2002).*
Sies H. et al. Nutritional Protection Against Skin Damage from Sunlight. Annual Review of Nutrition 24:173-200, 2004. (Year: 2004).*

\* cited by examiner

*Primary Examiner* — Ralph J Gitomer
(74) *Attorney, Agent, or Firm* — Patnstr® APC; Peter Jon Gluck, Esq.

(57) ABSTRACT

Diverse antioxidant supplements boost humans' ability to combat exposure to ultraviolet radiation (without being a substitute for sunscreen) and may be delivered effectively with many vehicles, enhancing user compliance.

3 Claims, 1 Drawing Sheet

Supplement Facts:

75 Liquid Soft Gels/Serving Size 3

Ingredients:

Fish Oil- 900 mg (18% EPA, 12% DHA)

Vitamin A (Beta Carotene-Mixed Carotenoids)- 10,000 IU

Vitamin D3- 1200 IU

Vitamin E-150 IU

Vitamin C- 150 mg

Green Tea Extract-600 mg

Pomegranate Extract-300 mg

Astaxanthin (Bioastin) 3mg

Zinc-15 mg

Copper-1 mg

Selenium-75mcg

Tyrosine-150 mg

Phenylalanine-75 mg

Bioperine Complex-6 mg

HEALTHY TAN TYPE OF ANTIOXIDANT DEFENSE

CROSS REFERENCE TO RELATED APPLICATIONS

This application claims the benefit of and priority to U.S. Provisional Patent Application Ser. No. 62/396,014 filed Sep. 16, 2016, the content of which is incorporated herein by reference herein in its entirety.

BACKGROUND

This disclosure relates to exogenous supplements used to support or bolster the body's own natural defenses. In particular, the instant disclosures provide a diverse antioxidant supplement to boost the body's natural defenses against ultraviolet radiation. While certain types of liquid softgels are an initial embodiment, other delivery systems are contemplated and described according to the instant teachings.

Without being a substitute for sunscreen, the instant formulations comprise a diverse antioxidant supplement to boost the body's natural defenses against ultraviolet radiation.

The present inventor has noted myriad compounds and moieties having antioxidant effects against various challenges to the body.

Empirical and pre-clinical testing shows unexpected benefits from the combination described below, and claimed herein.

As long as humans and other fair-skinned mammals are exposed to ultraviolet radiation, anything to mitigate deleterious impacts, from cancer to benign uncontrolled cellular mitosis, is an urgency. The present inventions fill the void comprising desiderata for said long unrequited need, it is respectfully proposed, and teach unique solutions, it is respectfully submitted.

OBJECTS AND SUMMARY OF THE INVENTION

Briefly stated, without being a substitute for sunscreen, the instant formulations comprise a diverse antioxidant supplement to boost the body's natural defenses against ultraviolet radiation.

According to embodiments there is provided a supplement comprising, in combination all of the ingredients of FIG. 1.

According to embodiments there is provided a supplement comprising, in combination all of the ingredients of FIG. 1, compounded in capsules.

According to embodiments there is provided a supplement comprising, in combination all of the ingredients of FIG. 1, compounded in soft gels.

According to embodiments there is provided a supplement comprising, in combination all of the ingredients of FIG. 1, compounded in liquid soft gels.

According to embodiments there is provided a supplement comprising, in combination all of the ingredients of FIG. 1, compounded in sublingual caplets.

According to embodiments there is provided a supplement comprising, in combination all of the ingredients of FIG. 1, compounded in alternate delivery vehicles.

According to embodiments there is provided a supplement comprising, in combination all of the ingredients of FIG. 1, compounded in transdermal patches.

BRIEF DESCRIPTION OF THE DRAWINGS

Various preferred embodiments are described herein with references to the drawings in which merely illustrative views are offered for consideration, whereby:

FIG. 1 is a list of the ingredients in the subject disclosures, and further data showing how this first example is formulated to deliver according to the instant teachings.

DETAILED DESCRIPTION

The present inventor has been observing outdoor and related UV-light exposing activities and concluded that a number of known and studied ingredients in combination can help mitigate said exposure.

The present inventor has formulated and tested numerous approaches to improvements in absorption and onset functions of plethoric groups and families of compounds. The Appendix to the provisional application comprises a list of ingredients for the subject formulations as planned to be licensed by the FDA and California Dept. of Health to be manufactured, wholesaled, and/or repackaged by the present inventor/assignee and/or his delegates.

Many of these chemical entities, compounds and families have been profiled, and research has demonstrated unexpected benefits of delivering them either in tablet, capsule form or sublingually. Accordingly, the present inventor has outlined testing and formulation/application related lower dosages of select compounds and achieved unexpectedly better results—as explained herein, and claimed below.

Preferred dosage form, as indicated in Example One/FIGURE one is Liquid Soft Gels. These could comprise a serving size of three per diem, and be manufactured on existing systems, with the previously approved and used materials creating no barriers to entry, on knowledge of the inventor.

Those skilled in the art appreciate that application specific delivery drives the best way to impart chemicals to living systems—accordingly, the instant approach includes all other oral delivery means, including inhalables and suppositories. Sublinguals have also proven to be quite helpful for certain families of compounds.

Expressly incorporated by this reference, as if fully set forth herein in their entirety, are the following patents and publication: U.S. Pat. Nos. 5,260,440; 6,316,460; 6,002,021; U.S. Pat. Nos. 4,444,784; 5,159,104; 6,100,407; EP 1 171 134; PCT/US2000/00662; U.S. Pat. Nos. 8,497,370; 7,279,457, 3,428,728; 8,201,503; EP 1 019 039; US 2014/0011755; US 2013/0143894; US 2013/0059854; US 2010/0209359; US 2010/0113453; US 2010/0069397; US 2007/0122355; US 2006/0099300; US 2003/0073133; US 2003/0022912; U.S. Pat. Nos. 8,293,295; 7,449,175; 7,329,416; 7,258,850; 6,903,127; 6,632,419; 6,592,850; 6,552,024; 6,548,490; 6,531,114; 6,428,769; 6,403,597; 6,342,251; 6,211,156; 6,200,591; WO 2005/039530A1; WO 00/54777A1; EP 2,452,675A1; EP 1,536,769A2; EP 960,921A2; EP 1,171,134A1; DE 19834505A1; AU 3744800A; CN101683325A; CN10157930A; CN100488509C; CN101224222A; CN101057850A; U.S. Pat. Nos. 8,563,534; 8,501,715; 8,481,570; 8,211,922; 8,158,611; 7,279,459; 7,186,704; GB 2497728A; CN 101991854A; U.S. Pat. Nos. 8,012,503; 7,163,705; CN 001600159A; US 2013/0123354; U.S. Pat. No. 7,138,107; and, U.S. Pat. No. 6,849,649.

Another important area is controlled release as, previously available controlled release had a number of deficiencies. The present invention provides some potential in alternate formats to addresses these deficiencies. This invention may be particularly applicable to a number of compounds, as shown by work done with, for example, extremely low dosages of active. The practice of this invention using sub-compounds is desired since increasing the bioavailability of this drug is useful in the treatment of pulmonary hypertension, and psychogenic impotence. Further, this invention allows for the successful use of lower concentrations of this drug without major side effects occurring which are extremely undesirable. Other things added to each alternate formulation, as known to those skilled in the art are herein offered for consideration.

Formulations including an active agent, such as insulin, and one or more excipients, such as a chelator and/or solubilizing agent, that dissolve rapidly in aqueous media are likewise described herein, and contemplated by the instant teachings. In select embodiments, the formulations are suitable for subcutaneous or sublingual administration. These formulations are rapidly absorbed through mucosal surfaces (parenteral, pulmonary, etc.) and through the fatty tissue when administered subcutaneously. This is achieved through the addition of excipients, especially solubilizers such as acids and metal chelators.

As generally used herein, a drug is considered "highly soluble" when the highest dose strength is soluble in 250 ml or less of aqueous media over the pH range of 1-7.5. The volume estimate of 250 ml is derived from typical bioequivalence (BE) study protocols that prescribe administration of a drug product to fasting human volunteers with a glass (about 8 ounces) of water. A drug is considered highly soluble when 90% or more of an administered dose, based on a mass determination or in comparison to an intravenous reference dose, is dissolved. Solubility can be measured by the shake-flask or titration method or analysis by a validated stability-indicating assay.

As generally used herein, an immediate release drug formulation is considered "rapidly dissolving" when no less than 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer, and (3) a pH 6.8 buffer or Simulated Intestinal Fluid USP without enzymes.

Although described with reference to small-molecule moieties like insulin, the instant formulations may be used with other agents, including peptides, proteins, nucleotide molecules (RNA sequences, DNA sequences), sugars, polysaccharides, and small organic molecules. In some examples, the active agent is at least slightly soluble in aqueous medium (i.e. 10,000 parts of aqueous solvent per solute), and in others, is highly soluble in aqueous medium. Preferably the active agent is highly potent, so that only a small amount (e.g. in the microgram range) is needed to provide a therapeutic effect. Suitable peptides include but are not limited to insulin and derivatives of insulin, such as lispro; C-peptide; glucagon-like peptide 1 (GLP 1) and all active fragments thereof; human amylin and synthetic forms of amylin, such as pramlintide; parathyroid hormone (PTH) and active fragments thereof (e.g. PTH1-34); calcitonin; human growth hormone (HGH); erythropoietin (EPO); macrophage-colony stimulating factor (M-CSF); granulocyte-macrophage-colony stimulating factor (GM-CSF); and interleukins. In the preferred embodiment the active agent is insulin. Suitable small molecules include nitroglycerin, sumatriptan, narcotics (e.g. fentanyl, codeine, propoxyphene, hydrocodone, and oxycodone), benzodiazepines (e.g. Alprazolam, Clobazam, Clonazepam, Diazepam Flunitrazepam, Lorazepam, Nitrazepam, Oxazepam, Temazepam, and Triazolam), phenothiazines (Chlorpromazine, Fluphenazine, Mesoridazine, Methotrimeprazine, Pericyazine, Perphenazine, Prochlorperazine, Thioproperazine, Thioridazine, and Trifluoperazine), and selective serotonin reuptake inhibitors (SSRIs) (e.g. sertraline, fluvoxamine, fluoxetine, citalopram, and paroxetine).

The dosages of the active agents depend on their bioavailability and the condition, ailment, disease or disorder to be treated. The compositions optionally contain one or more excipients.

In select embodiments, one or more solubilizing agents are included with the active agent to promote rapid dissolution in aqueous media. Suitable solubilizing agents include wetting agents such as polysorbates and poloxamers, non-ionic and ionic surfactants, food acids and bases (e.g. sodium bicarbonate), and alcohols, and buffer salts for pH control. Suitable acids include acetic acid, ascorbic acid, citric acid, and hydrochloric acid. For example, if the active agent is insulin, a preferred solubilizing agent is citric acid, as known to those skilled in the art.

Diluents, also referred to herein as fillers, are typically necessary to increase the bulk of a solid dosage form so that a practical size is provided for compression of tablets or formation of beads and granules. Suitable fillers include, but are not limited to, dicalcium phosphate dihydrate, calcium sulfate, lactose, sucrose, mannitol, sorbitol, cellulose, microcrystalline cellulose, powdered cellulose, kaolin, sodium chloride, dry starch, hydrolyzed starches, pregelatinized starch, silicone dioxide, titanium oxide, magnesium aluminum silicate, calcium carbonate, compressible sugar, sugar spheres, powdered (confectioner's) sugar, dextrates, dextrin, dextrose, dibasic calcium phosphate dehydrate, glyceryl palmitostearate, magnesium carbonate, magnesium oxide, maltodextrin, polymethacrylates, potassium chloride, talc, and tribasic calcium phosphate.

Binds are used to impart cohesive qualities to a solid dosage formulations, and thus ensure that a tablet, bead or granule remains intact after the formation of the dosage forms. Suitable binder materials include, but are not limited to, starch, pregelatinized starch, gelatin, sugars (including sucrose, glucose, dextrose, lactose and sorbitol), dextrin, maltodextrin, zein, polyethylene glycol, waxes, natural and synthetic gums such as acacia, guar gum, tragacanth, alginate, sodium alginate, celluloses, including hydroxypropylmethylcellulose, carboxymethylcellulose sodium, hydroxypropylcellulose, hydroxylethylcellulose, ethyl cellulose, methyl cellulose, and veegum, hydrogenated vegetable oil, Type I, magnesium aluminum silicate, and synthetic polymers such as acrylic acid and methacrylic acid copolymers, carbomer, methacrylic acid copolymers, methyl methacrylate copolymers, aminoalkyl methacrylate copolymers, polyacrylic acid/polymethacrylic acid, and polyvinylpyrrolidone.

Lubricants are used to facilitate soft gel, capsule and/or tablet/caplet manufacture. Examples of suitable lubricants include, but are not limited to, magnesium stearate, calcium stearate, stearic acid, glyceryl behenate, glyceryl monostearate, glyceryl palmitostearate, hydrogenated castor oil, hydrogenated vegetable oil, type I, sodium benzoate, sodium lauryl sulfate, sodium stearyl fumarate, polyethylene glycol, talc, zinc stearate, and mineral oil and light mineral oil.

Stabilizers are used to inhibit or retard drug decomposition reactions which includes, by way of example, oxidative reactions. A number of stabilizers may be used.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

If desired, the tablets, wafers, films, lozenges, beads, granules, or particles may also contain minor amount of nontoxic auxiliary substances such as dyes, masking agents, sweeteners, coloring and flavoring agents, pH buffering agents, or preservatives.

Blending or copolymerization sufficient to provide a certain amount of hydrophilic character can be useful to improve wettability of the materials. The active compounds (or pharmaceutically acceptable salts thereof) may be administered in the form of a pharmaceutical composition wherein the active compound(s) is in admixture or mixture with one or more pharmaceutically acceptable carriers, excipients or diluents. Suitable dosage forms include powders, films, wafers, lozenges, capsules, and tablets. Following administration, the dosage form dissolves quickly releasing the drug or forming small particles containing drug, optionally containing one or more excipients.

It is known that oral medicines are particularly desirable and sought after discreet form of treatment for sexual dysfunction. Recently, the oral use of the citrate salt of sildenafil has been approved by the U.S. Food and Drug Administration (FDA) for the treatment of male erectile dysfunction. Sildenafil is reported to be a selective inhibitor of cyclic-GMP-specific phosphodiesterase type 5 (PDE5), the predominant isozyme metabolizing cyclic GMP formed in the corpus cavernosum. Since sildenafil is a potent inhibitor of PDE5 in the corpus cavernosum, it is believed to enhance the effect of nitric oxide release. Inasmuch as sildenafil at the currently recommended doses of 25-100 mg has little effect in the absence of sexual stimulation, sildenafil is believed to restore the natural erectile response to sexual stimulation but not cause erections in the absence of such stimulation. The localized mechanism by which cyclic GMP stimulates relaxation of the smooth muscles has not been elucidated.

The term "controlled release" when applied to anything delivered is also important. Softgels, caplets/capsules or sublingual tablets is limited to a maximum of about 60 minutes. Traditional sublingual tablets are usually designed as water soluble tablets made of water soluble sugars such as sorbitol, lactose, mannitol, etc. In the literature, controlled release sublingual tablets are very scarce, U.S. Pat. No. 3,428,728 to Lowey (1969) describes a controlled release sublingual tablet made by cooking gum acacia and sorbitol (by heating) till partial dryness followed by addition of citric acid, color and flavor followed by cooling. Active ingredients such as nitroglycerin, caffeine, guaiocolate, amylase or isoproterenol were then added to the pourable paste that was cast into tablets. However, Lowey's discovery cannot be applied to make tablets by compression. The time of release for a pharmaceutical preparation is critical to the effectiveness of the drug. The sublingual tablet of the present invention can be prepared by compression methods and provides a controlled drug release, in contradistinction to the prior art.

The terms excipients or "pharmaceutically acceptable carrier or excipients" and "bio-available carriers or excipients" above-mentioned include any appropriate compounds known to be used for preparing the dosage form, such as the solvent, the dispersing agent, the coating, an anti-bacterial or anti-fungal agent and a preserving agent or the delayed absorbent. Usually, such kind of carrier or excipient does not have therapeutic activity itself. Each formulation prepared by combining the derivatives disclosed in the present invention and the pharmaceutically acceptable carriers or excipients will not cause the undesired effect, allergy or other inappropriate effects while being administered to an animal or human. Numerous compounds formulated according to the instant process have been formulated for those in need and others can be made so based upon the processes perfected herein.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for mitigating damage from ultraviolet light exposure to skin in a subject in need thereof by orally administering an effective dose of a composition consisting essentially of:
   Fish oil;
   Vitamins A, D3, E, and C;
   Green tea extract;
   Pomegranate fruit extract;
   Astaxanthinn and/or Biostatin;
   Zinc;
   Copper;
   Tyrosine;
   Phenylalanine; and
   Bioperine Complex.

2. A method for mitigating damage from ultraviolet light exposure to skin in a subject in need thereof by oral mucosally administering an effective dose of a composition consisting essentially of:
   Fish oil;
   Vitamins A, D3, E, and C;
   Green tea extract;
   Pomegranate fruit extract;
   Astaxanthinn and/or Biostatin;
   Zinc;
   Copper;
   Tyrosine;
   Phenylalanine; and
   Bioperine Complex.

3. A method for mitigating damage from ultraviolet light exposure to skin in a subject in need thereof orally administering capsules, pills, or sublingual vehicles administering an effective dose of a composition consisting essentially of:
   Fish oil;
   Vitamins A, D3, E, and C;
   Green tea extract;
   Pomegranate fruit extract;
   Astaxanthinn and/or Biostatin;
   Zinc;
   Copper;
   Tyrosine;
   Phenylalanine; and
   Bioperine Complex.

* * * * *